(12) United States Patent
Liu et al.

(10) Patent No.: US 12,071,674 B2
(45) Date of Patent: Aug. 27, 2024

(54) NUCLEIC ACID PROBE SET AND NUCLEIC ACID LATERAL FLOW IMMUNOASSAY HAVING THE SAME

(71) Applicant: National Defense Medical Center, Taipei (TW)

(72) Inventors: Cheng-Che Liu, Taipei (TW); Po-Da Hong, Taipei (TW); Yi-Huei Huang, Taipei (TW); Kuan-Yi Yu, Taipei (TW); Shou-Ping Huang, Taipei (TW); Shou-Hung Tang, Taipei (TW); Juin-Hong Cherng, Taipei (TW)

(73) Assignee: National Defense Medical Center, Taipei (TW)

( * ) Notice: Subject to any disclaimer, the term of this patent is extended or adjusted under 35 U.S.C. 154(b) by 305 days.

(21) Appl. No.: 17/355,623

(22) Filed: Jun. 23, 2021

(65) Prior Publication Data
US 2022/0298588 A1     Sep. 22, 2022

(30) Foreign Application Priority Data
Mar. 17, 2021    (TW) .................. 110109507

(51) Int. Cl.
| | |
|---|---|
| *C12Q 1/6804* | (2018.01) |
| *C12Q 1/6813* | (2018.01) |
| *C12Q 1/70* | (2006.01) |
| *G01N 33/53* | (2006.01) |
| *B01L 3/00* | (2006.01) |

(52) U.S. Cl.
CPC ........... *C12Q 1/701* (2013.01); *C12Q 1/6804* (2013.01); *C12Q 1/6813* (2013.01); *C12Q 1/70* (2013.01); *G01N 33/5308* (2013.01); *B01L 3/5027* (2013.01); *B01L 3/502715* (2013.01); *G01N 2333/025* (2013.01)

(58) Field of Classification Search
CPC ............................ C12Q 1/70; C12Q 2565/50; C12Q 2565/625; G01N 2333/025
See application file for complete search history.

(56) References Cited

FOREIGN PATENT DOCUMENTS

| | | |
|---|---|---|
| CN | 110423844 A | 11/2019 |
| TW | 201520553 A | 6/2015 |

OTHER PUBLICATIONS

Mao et al., "Disposable Nucleic Acid Biosensors Based on Gold Nanoparticle Probes and Lateral Flow Strip," Analytical Chemistry, vol. 81, pp. 1660-1668. (Year: 2009).*
Hoffman et al., "Marked Variability of BK Virus Load Measurement Using Quantitative Real-Time PCR among Commonly Used Assays," Journal of Clinical Microbiology, August, vol. 46, No. 8, pp. 2671-2680. (Year: 2008).*
Huang et al., "Development of a Nucleic Acid Lateral Flow Immunoassay for the Detection of Human Polyomavirus BK," Diagnostics, vol. 10, pp. 1-14. (Year: 2020).*
Huang et al., Development of a Nucleic Acid Lateral Flow Immunoassay for the Detection of Human Polyomavirus BK, Diagnostics, 2020, 10, 403, p. 1-14.

* cited by examiner

*Primary Examiner* — Young J Kim
(74) *Attorney, Agent, or Firm* — ANOVA LAW GROUP, PLLC

(57) ABSTRACT

A nucleic acid probe set is disclosed. The nucleic acid probe set comprises a detection probe and a capture probe, and the detection probe and the capture probe both include a nucleotide sequence that is extracted from a conserved region of a genome sequence belong to a BK virus. A nucleic acid lateral flow immunoassay for using in detection of BK virus is also disclosed. The nucleic acid lateral flow immunoassay comprises: the forgoing nucleic acid probe set, a test strip, and a streptavidin (SA) solution. Experimental data have proved that, the nucleic acid lateral flow immunoassay can be adopted for conducting a BK virus detection on a sample that is collected from environmental water, sewage water, drinking water, urine, or serum.

15 Claims, 8 Drawing Sheets
Specification includes a Sequence Listing.

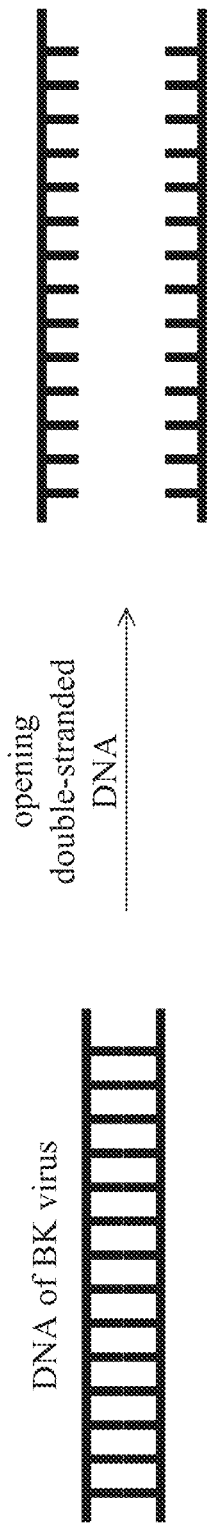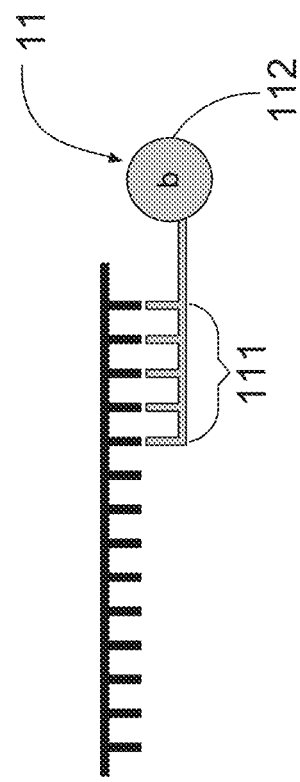
FIG. 3A
FIG. 3B

```
                              SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: BK Virus_BK4 p0001

<400> SEQUENCE: 1
tcacatagac tccgaagac                                                      19

<210> SEQ ID NO 2
<211> LENGTH: 19
<212> TYPE: DNA
<213> ORGANISM: Artificial Sequence
<220> FEATURE:
<223> OTHER INFORMATION: BK Virus_BK4 p0002

<400> SEQUENCE: 2
ccgactttaa cgacgaccc                                                      19

<210> SEQ ID NO 3
<211> LENGTH: 20
<212> TYPE: DNA
<213> ORGANISM: Artificial Sequence
<220> FEATURE:
<223> OTHER INFORMATION: BK Virus_BK5 p001

<400> SEQUENCE: 3
cgcattgagg agtttgtata                                                     20

<210> SEQ ID NO 4
<211> LENGTH: 19
<212> TYPE: DNA
<213> ORGANISM: Artificial Sequence
<220> FEATURE:
<223> OTHER INFORMATION: BK Virus_BK5 p0002

<400> SEQUENCE: 4
cgacattaac gaccacgag                                                      19

<210> SEQ ID NO 5
<211> LENGTH: 20
<212> TYPE: DNA
<213> ORGANISM: Artificial Sequence
<220> FEATURE:
<223> OTHER INFORMATION: BK Virus_BK7 p01

<400> SEQUENCE: 5
tcttttttga taacgggtc                                                      20

<210> SEQ ID NO 6
<211> LENGTH: 20
<212> TYPE: DNA
<213> ORGANISM: Artificial Sequence
<220> FEATURE:
<223> OTHER INFORMATION: BK Virus_BK7 p02

<400> SEQUENCE: 6
```

```
attagtttct tgacgaggag                                                      20

<210> SEQ ID NO 7
<211> LENGTH: 23
<212> TYPE: DNA
<213> ORGANISM: Artificial Sequence
<220> FEATURE:
<223> OTHER INFORMATION: BK Virus_BK12 P60011

<400> SEQUENCE: 7
tatgtatgaa tagagtctta ggt                                                  23

<210> SEQ ID NO 8
<211> LENGTH: 22
<212> TYPE: DNA
<213> ORGANISM: Artificial Sequence
<220> FEATURE:
<223> OTHER INFORMATION: BK Virus_BK12 P60012

<400> SEQUENCE: 8
gaaaggaagg taagttgtta ag                                                   22

<210> SEQ ID NO 9
<211> LENGTH: 23
<212> TYPE: DNA
<213> ORGANISM: Artificial Sequence
<220> FEATURE:
<223> OTHER INFORMATION: BK Virus_detection probe

<400> SEQUENCE: 9
tatgtatgaa tagagtctta ggt                                                  23

<210> SEQ ID NO 10
<211> LENGTH: 23
<212> TYPE: DNA
<213> ORGANISM: Artificial Sequence
<220> FEATURE:
<223> OTHER INFORMATION: BK Virus_detection probe

<400> SEQUENCE: 10
tatgtatgaa tagagtctta ggt                                                  23

<210> SEQ ID NO 11
<211> LENGTH: 22
<212> TYPE: DNA
<213> ORGANISM: Artificial Sequence
<220> FEATURE:
<223> OTHER INFORMATION: BK Virus_capture probe

<400> SEQUENCE: 11
gaaaggaagg taagttgtta ag                                                   22

<210> SEQ ID NO 12
<211> LENGTH: 22
<212> TYPE: DNA
<213> ORGANISM: Artificial Sequence
<220> FEATURE:
<223> OTHER INFORMATION: BK Virus_capture probe

<400> SEQUENCE: 12
gaaaggaagg taagttgtta ag                                                   22
```

NUCLEIC ACID PROBE SET AND NUCLEIC ACID LATERAL FLOW IMMUNOASSAY HAVING THE SAME

REFERENCE TO AN ELECTRONIC SEQUENCE LISTING

The contents of the electronic sequence listing (13055sequencelisting_ST25.txt; Size: 3 kilobytes; and Date of Creation: Sep. 29, 2021) is herein incorporated by reference in its entirety.

BACKGROUND OF THE INVENTION

1. Field of the Invention

The present invention relates to the technology field of virus detection, and more particularly to a nucleic acid probe set and a nucleic acid lateral flow immunoassay using the same.

2. Description of the Prior Art

It has been known that, BK virus (BKV), JC virus (JCV) and simian virus (SV) are three of human polyomaviruses since their genomes share 70-75% sequence similarity. In which, BKV is a small (~45 nm), icosahedral, non-enveloped double stranded DNA virus composed of about 5,100 base pairs. As described in more detail below, BKV is a ubiquitous polyomavirus that is often acquired during early childhood. It lies dormant in the genitourinary tract, but can be reactivated in certain immunocompromised diseases states. In recent years, the clinical cases have reported that, BKV is a common infection encountered after kidney transplantation. Moreover, BKV is associated with a spectrum of manifestations, starting with sub-clinical viruria, followed by viremia and BKV-associated nephropathy. For above reasons, early detection of BKV infection for a patient before a kidney transplant is necessary in order to significantly reduce the risk of BKV infection. In addition, it is also necessary for the patient who has been received the kidney transplant to receive a regular post-transplant BKV detection.

The BKV genome can be divided into three regions: noncoding control region (NCCR) of approximately 0.4 kb, viral early gene region of approximately 2.3 kb and viral late gene region of approximately 2.4 kb. The viral late gene region encodes the capsid proteins VP1, VP2 and VP3 as well as the BKV agnoprotein. Currently, there are three common clinic methods for achieving the BKV detection: (1) Polymerase chain reaction (PCR) analysis of BKV DNA levels in urine or serum, (2) PCR analysis of BKV VP1 mRNA levels in urine or serum, and (3) microscopic analysis of urinary decoy cells. Bioengineers skilled in virus detections should know that, PCR method shows drawbacks of time-consuming to conduct, high cost, and must conducted by a professional personnel through operating a PCR machine.

On the other hand, the microscopic analysis of urinary decoy cells commonly comprising following operation steps:

S1: collecting a urine sample;
S2: centrifuging the urine sample for obtaining a precipitation, and then making the precipitation to a smear; and
S3: using an optical microscope to observe variations of cell morphology features from the smear.

Clinical experiences have indicated that, the microscopic analysis of urinary decoy cells often shows false negative when applying in BKV detection. In view of that, literature 1 discloses an improved BKV detection method using CRISPR. Literature 1, written by Kaminski et. al, is entitled with "A CRISPR-based assay for the detection of opportunistic infections post-transplantation and for the monitoring of transplant rejection", and is published on Nature Biomedical Engineering, vol. 4, pp. 601-609(2020). The improved BKV detection method comprises following operation steps:

(a) isolating DNA from blood sample and urine sample;
(b) applying a recombinase polymerase amplification (RPA) process to the products of the forgoing step (a);
(c) completing an in-vitro RNA transcription of the products of the forgoing step (b) by using T7 polymerase, so as to obtain a target RNA; and
(d) making a CRISPR guide RNA (crRNA) be linked to the target RNA; and
(e) dropping the product of the forgoing step (d) to a lateral flow strip, and then using a reader to verify a T/C ratio value from the lateral flow strip.

It needs to particularly explain that, above-mentioned steps (a)-(e) are summarized from the disclosure of the literature 1. Moreover, after fully reading the literature 1's content, it is clear that, when adopting the disclosed BKV detection method using CRISPR and a lateral flow strip to carry out a BKV detection, a polymerase amplification process and a RNA transcription process are both needed to be conducted. However, bioengineers skilled in virus detections should know that, the polymerase amplification process and the RNA transcription process are certainly conducted by professional personnel through operating a PCR machine. Therefore, the disclosed BKV detection method using CRISPR still includes drawbacks of time-consuming to conduct, high cost, and certainly conducted by the professional personnel and operating a PCR machine.

From above descriptions, it is understood that there are still rooms for improvement in the conventional BKV detection methods. In view of that, inventors of the present application have made great efforts to make inventive research and eventually provided a nucleic acid probe set and a nucleic acid lateral flow immunoassay using the same.

SUMMARY OF THE INVENTION

The primary objective of the present invention is to disclose a nucleic acid probe set, comprising a detection probe and a capture probe. The detection probe comprises a nucleotide sequence that is extracted from a conserved region of a genome sequence belong to a BK virus, and further comprises a labeling connected to a terminal base of the nucleotide sequence. On the other hand, the capture probe also comprises the same nucleotide sequence and a combiner connected to a terminal base of the nucleotide sequence, wherein the combiner is adopted for combining with a tetrameric protein such as streptavidin. Therefore, a nucleic acid lateral flow immunoassay for detection of BK virus is developed, and comprises: the nucleic acid probe set, a test strip, and the streptavidin. Experimental data have proved that, the nucleic acid lateral flow immunoassay can achieve the detection of BK virus from a sample that is collected from environmental water, sewage water, drinking water, urine, or serum.

It is worth mentioning that, when adopting the nucleic acid lateral flow immunoassay of the present invention to carry out a BKV detection, a sample for the BKV detection is not needed to be applied with a PCR process and/or an RPA process. Moreover, there is no RNA transcription process conducted during the operation of the BKV detection. Therefore, the nucleic acid lateral flow immunoassay disclosed by the present invention includes advantages of low cost, achieving rapid BKV detection, and able to be conducted by common people, able to be used in BKV detection without needing using any professional machine.

In order to achieve the primary objective of the present invention, the present invention provides an embodiment of the nucleic acid probe set, comprising:

a capture probe, comprising a first primer that comprises at least 19 bases and a combiner connected to one terminal base of the first primer; and a detection probe, comprising a second primer that comprises at least 19 bases and a labeling connected to one terminal base of the second primer;

wherein the first primer and the second primer are both a nucleotide sequence that is extracted from a conserved region of a genome sequence belong to a BK virus.

In one embodiment, the combiner is a biotin that is used to combine with a streptavidin (SA), and the labeling is made of a fluorescent material that is selected from a group consisting of gold nanoparticles, silver nanoparticles, carbon nanoparticles, quantum dots (QDs), colloidal gold, colloidal silver, and colloidal QDs.

In one embodiment, the nucleotide sequence is selected from a group consisting of 5'-GAAAGGAAGGTAAGTTGTTAAG-3' (SEQ ID NO:8) and 5'-TATGTATGAATAGAGTCTTAGGT-3' (SEQ ID NO:7).

In one embodiment, the terminal base of the first primer connected with the combiner is a front-terminal base or a rear-terminal base, the terminal base of the second primer connected with the labeling is a front-terminal base or a rear-terminal base.

In one embodiment, the capture probe further comprises a spacer that is connected between the terminal base and the combiner, and the spacer comprises 10 adenines.

In one embodiment, the detection probe further comprises a spacer connected to the terminal base and a thiol group connected between the spacer and the labeling, and the spacer comprises 10 adenines.

In one embodiment, the labeling is made of gold nanoparticles having a particle size in a range between 25 nm and 65 nm.

Moreover, the present invention also disclosed a nucleic acid lateral flow immunoassay, comprising:

a capture probe, comprising a first primer that comprises at least 19 bases and a combiner connected to one terminal base of the first primer;

a detection probe, comprising a second primer that comprises at least 19 bases and a labeling connected to one terminal base of the second primer; wherein the first primer and the second primer are both a nucleotide sequence that is extracted from a conserved region of a genome sequence belong to a BK virus;

a lateral flow strip, comprising a membrane substrate that is formed with a test line made of a first capture antibody and a control line made of a second capture antibody thereon; and a tetrameric protein solution;

wherein when adopting the nucleic acid lateral flow immunoassay to carry out a BK virus detection, a sample having a DNA of the BK virus is heated firstly, and then the capture probe and the detection probe are mixed into the sample so as to obtain a test sample; subsequently, the test sample is added into the tetrameric protein solution so as to obtain a test solution; consequently, the lateral flow strip is disposed into the test solution, and an optical reader is operated to read out a T/C ratio value from a first colored line showing up in the test line and a second colored line showing up in the control line.

In one embodiment, the sample is selected from a group consisting of sample collected from an environmental water, sample collected from a sewage water, sample collected from a drinking water, sample collected from a urine, and sample collected from a serum.

In one embodiment, the tetrameric protein solution comprising a buffer liquid and a tetrameric protein dissolved or dispersed in the buffer liquid.

In one embodiment, the tetrameric protein is a streptavidin (SA), and the buffer liquid is a phosphate buffer solution.

In one embodiment, the lateral flow strip further comprises:

a supporting substrate, wherein the membrane substrate is disposed on the supporting substrate; and an absorption pad, being formed on the supporting substrate, and being located at a rear-end side of the supporting substrate.

In one embodiment, the membrane substrate is made of a material that is selected from a group consisting of nitrocellulos (NC), polyvinylidene difluoride (PVDF) and nylon.

In one embodiment, the combiner is a biotin.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 3A to FIG. 3E show schematic diagrams for describing a flow of adopting the nucleic acid lateral flow immunoassay to carry out a BK virus detection;

DETAILED DESCRIPTION OF THE PREFERRED EMBODIMENTS

To more clearly describe a nucleic acid probe set and a nucleic acid lateral flow immunoassay comprising the nucleic acid probe set according to the present invention, embodiments of the present invention will be described in detail with reference to the attached drawings hereinafter.

Nucleic Acid Probe Set

Figure 1:
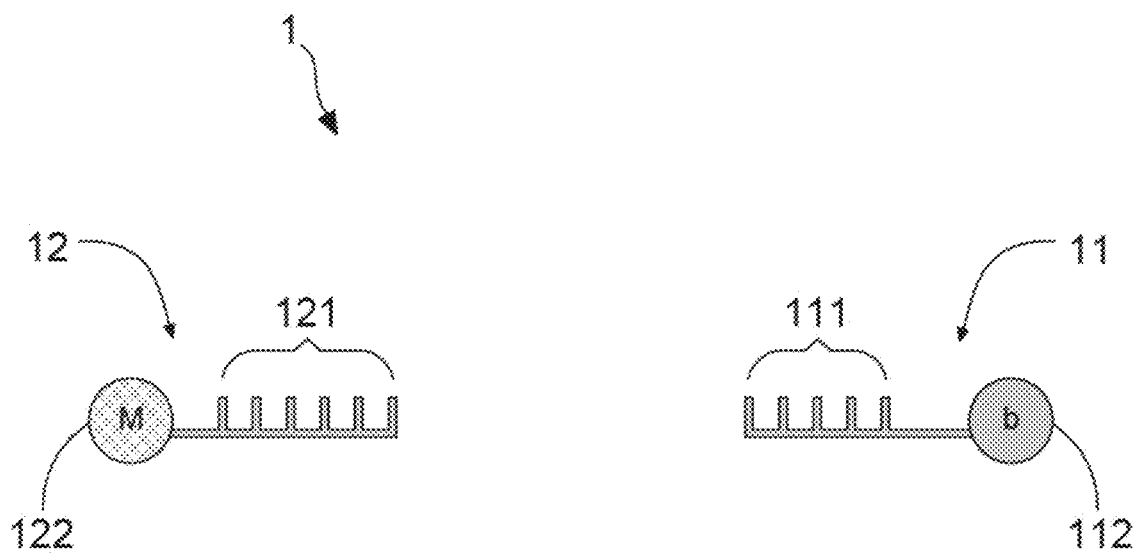
FIG. 1 shows a schematic diagram for describing a nucleic acid probe set according to the present invention.

With reference to FIG. 1, there is shown a schematic diagram for describing a nucleic acid probe set according to the present invention. As FIG. 1 shows, the nucleic acid probe set 1 comprises a capture probe 11 and a detection probe 12. The capture probe 11 comprises a first primer 111 that comprises at least 19 bases and a combiner 112 connected to one terminal base of the first primer 111, and the detection probe 12 comprises a second primer 121 that comprises at least 19 bases and a labeling 122 connected to one terminal base of the second primer 121. According to the present invention, the first primer 121 and the second primer 121 are both a nucleotide sequence that is extracted from a conserved region of a genome sequence belong to a BK virus. Moreover, in a specific embodiment, melting temperature ($T_m$) of the second primer 121 is greater than that of the first primer 111.

As explained in more detail below, the combiner 112 is a biotin that is used to combine with a streptavidin (SA), and the labeling 122 is made of a fluorescent material that is selected from a group consisting of gold nanoparticles, silver nanoparticles, carbon nanoparticles, quantum dots (QDs), colloidal gold, colloidal silver, and colloidal QDs.

Manufacture of the Nucleic Acid Probe Set

In one exemplary embodiment, method for extracting the aforesaid nucleotide sequence from a conserved region of a BK virus's genome sequence comprises following operation steps:

(a) collecting 232 genome sequences (i.e., a complete nucleotide sequence) of BKV, 464 genome sequences of JCV and 34 genome sequences of SV40 from DNA database of National Center for Biotechnology Information (NCBI);

(b) using DNASTAR Lasergene 8.0 to carry out a multiple sequence alignment between the 730 genome sequences, thereby finding out a consensus sequence;

(c) applying a conserved region identifying process to the 232 genome sequences of BKV, thereby finding out four conserved regions, including 987-1100 (114 bp), 1102-1210 (109 bp), 1809-1876 (68 bp), and 3306-3389 (84 bp);

(d) using Vector NTI Advance 11.0 to complete a primer design based the four conserved regions, therefore obtaining eight nucleotide sequences that are listed in following Table (1); and (f) synthesizing a plurality of capture probes 11 and a plurality of detection probes 12 by using the obtained eight nucleotide sequences.

TABLE (1)

| | Sequence |
|---|---|
| BK4 p0001 | 5'-TCACATAGACTCCGAAGAC-3' |
| BK4 p0002 | 5'-CCGACTTTAACGACGACCC-3' |
| BK5 p001 | 5'-CGCATTGAGGAGTTTGTATA-3' |
| BK5 p002 | 5'-CGACATTAACGACCACGAG-3' |
| BK7 p01 | 5'-TCTTTTTTGATAACGGGGTC-3' |
| BK7 p02 | 5'-ATTAGTTTCTTGACGAGGAG-3' |
| BK12 P60011 | 5'-TATGTATGAATAGAGTCTTAGGT-3' |

TABLE (1)-continued

| | Sequence |
|---|---|
| BK12 P60012 | 5'-GAAAGGAAGGTAAGTTGTTAAG-3' |

It needs to further explain that, the first primer 111 of the capture probe 11 can be any one of the nucleotide sequences listed in Table (1). Therefore, it is able to know that, the first primer 111 includes at least 19 bases. According to the present invention, the capture probe 11 further comprises a spacer that is connected between the terminal base and the combiner 112, wherein the forgoing terminal base is a front-terminal base or a rear-terminal base of the nucleotide sequence. Moreover, the spacer comprising 10 adenines, and has a notation of A10. On the other hand, the second primer 121 of the detection probe 12 can be any one of the nucleotide sequences listed in Table (1). Therefore, it is able to know that, the second primer 121 also includes at least 19 bases. According to the present invention, melting temperature ($T_m$) of the second primer 121 is greater than that of the first primer 111. In addition, the detection probe 12 further comprises a spacer (i.e., A10) connected to the terminal base and a thiol group connected between the spacer and the labeling 122.

After specificity tests of the synthesized capture probes 11 and the synthesized detection probes 12 are all completed, test result reveals that, the capture probe 11 containing the first primer 111 including nucleotide sequence of P60011 or P60012 exhibits outstanding specificity. Similarly, the detection probe 12 containing the second primer 121 including nucleotide sequence of P60011 or P60012 also shows outstanding specificity. As a result, there are two kinds of capture probes 11 and two kinds of detection probes 12 synthesized and listed in following Table (2).

TABLE (2)

| | Sequence (5'→3') |
|---|---|
| detection probe | HS-A10-TATGTATGAATAGAGTCTTAGGT |
| detection probe | TATGTATGAATAGAGTCTTAGGT-A10-SH |
| capture probe | Biotin-A10-GAAAGGAAGGTAAGTTGTTAAG |
| capture probe | GAAAGGAAGGTAAGTTGTTAAG-A10-Biotin |

Therefore, it is understood that, "A10" represents the spacer comprising 10 adenines, "HS" represents the thiol group, and "Biotin is the combiner 112 that is used to combine with a streptavidin (SA). Herein, it needs to particularly explain that, the labeling 122 is not shown in the two kinds of detection probes 12. In one exemplary embodiment, the labeling 122 can be made of gold nanoparticles having a particle size in a range between 25 nm and 65 nm.

Nucleic Acid Lateral Flow Immunoassay

Figure 2:
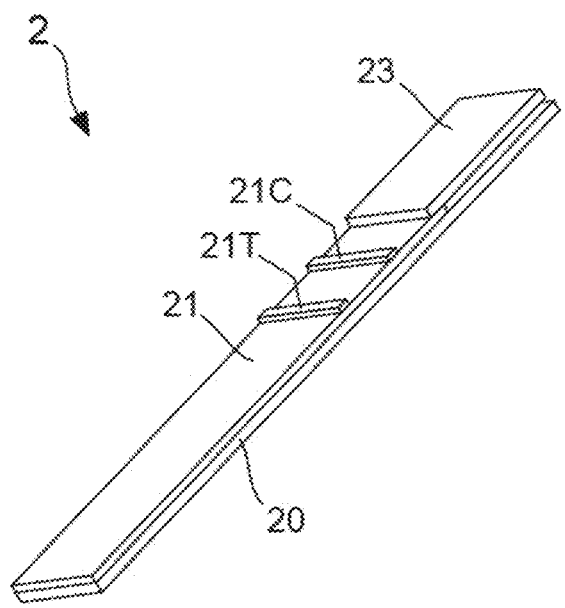
FIG. 2 shows a first schematic stereo diagram of a lateral flow strip of a nucleic acid lateral flow immunoassay according to the present invention.

According to the present invention, a nucleic acid lateral flow immunoassay comprising a nucleic acid probe set 1 as shown in FIG. 1 and a lateral flow strip is also disclosed. FIG. 2 shows a first schematic stereo diagram of the lateral flow strip of the nucleic acid lateral flow immunoassay according to the present invention. In one exemplary embodiment, as FIG. 2 shows, the lateral flow strip 2 comprises a supporting substrate 20, a membrane substrate 21 and an absorption pad 23. In which, the membrane substrate 21 can made of nitrocellulos (NC), polyvinylidene difluoride (PVDF) or nylon, and there are a test line 21T and a control line 21C formed on the membrane substrate 21. The test line 21T is formed by spraying a first solution containing a first capture antibody onto the membrane substrate 21, and the control line 21C is formed by spraying a second solution containing a second capture antibody onto the membrane substrate 21. In one embodiment, the first solution is made by dissolving or dispersing an anti-streptavidin antibody (i.e., the first capture antibody) in a PBS buffer, and the second solution is made by dissolving or dispersing an anti-BSA antibody (i.e., the second capture antibody) in a PBS buffer.

Figure 3C:
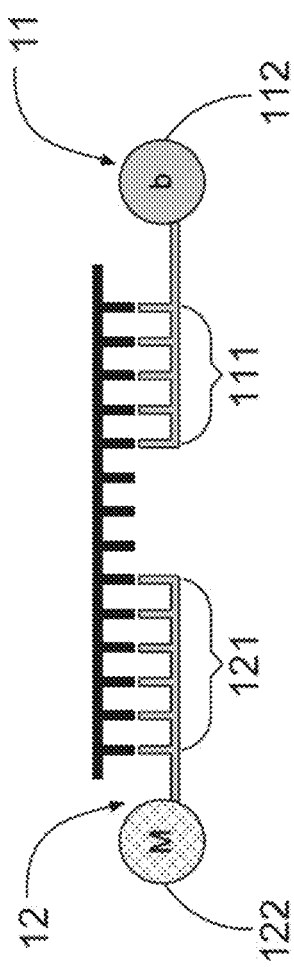
Figure 3D:
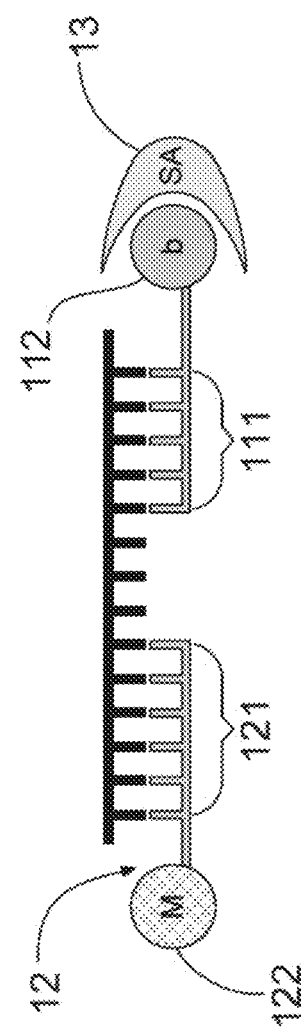
Figure 3E:
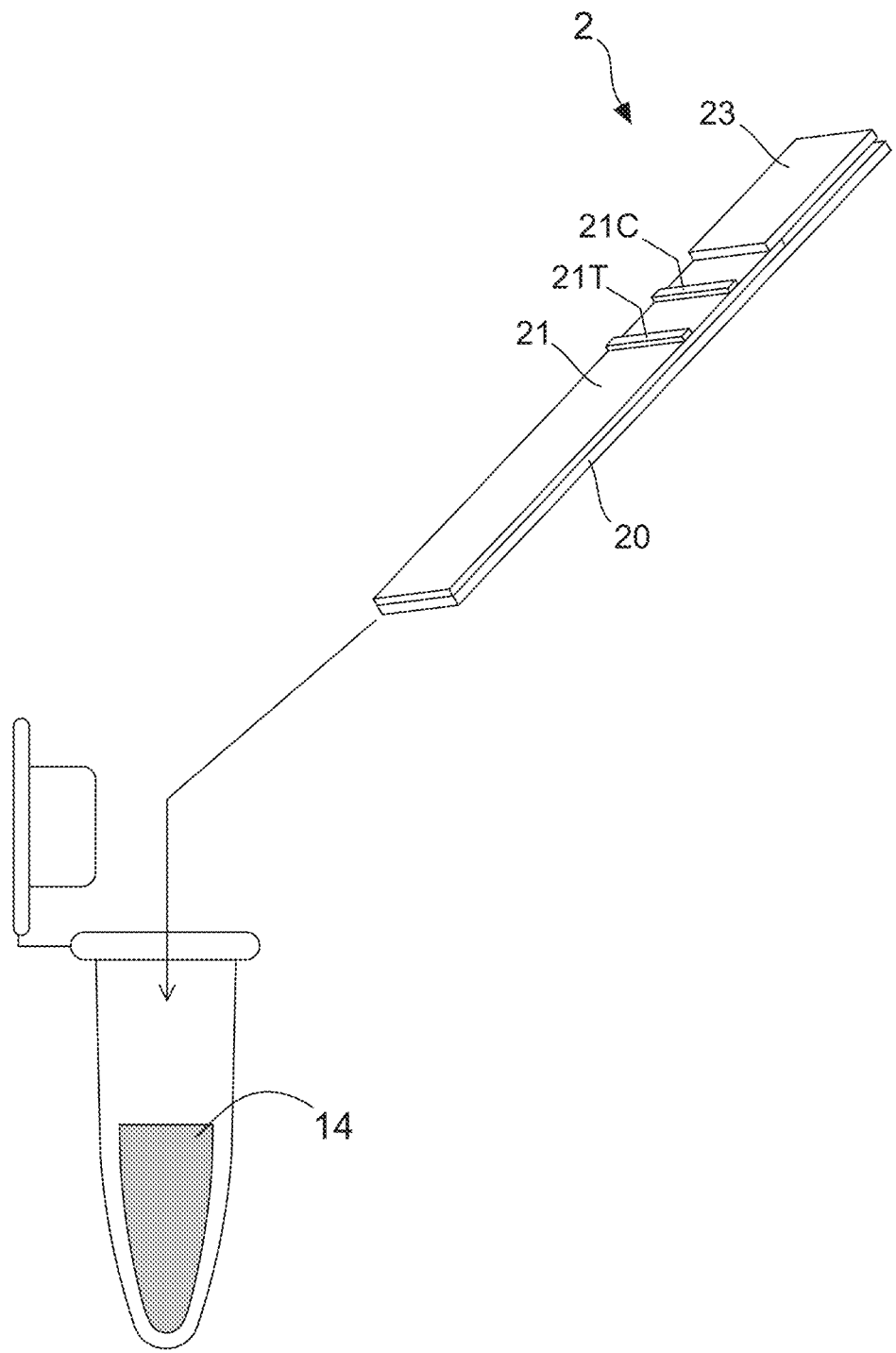

Adopting the Nucleic Acid Lateral Flow Immunoassay to Carry Out a BK Virus Detection FIG. 3A to FIG. 3E show schematic diagrams for describing a flow of adopting the nucleic acid lateral flow immunoassay to carry out a BK virus detection. A flow of using the nucleic acid lateral flow immunoassay to carry out a BK virus detection comprising following operation steps:

(1) As FIG. 3A shows, a sample containing BKV DNA is heated under a process temperature of 95° C for 2 minutes, thereby separating BKV'S double-stranded DNA into two single-stranded DNAs;

(2) As FIG. 3B shows, the capture probe 11 is mixed into the sample, so as to make the first primer 111 be connected to the single-stranded DNA;

(3) As FIG. 3C shows, the detection 12 is mixed into the sample, thereby making the second primer 121 be connected to the same single-stranded DNA;

(4) As FIG. 3D shows, producing a tetrameric protein solution by dissolving or dispersing a streptavidin (i.e., tetrameric protein) in a PBS buffer, and then adding the tetrameric protein solution into the sample for making the combiner 112 of the capture probe 11 combine with the streptavidin 13, thereby obtaining a test sample; and (5) As FIG. 3E shows, disposing lateral flow strip 2 into the test solution 14, and then using an optical reader to read out a T/C ratio value from a first colored line showing up in the test line 21T and a second colored line showing up in the control line 21C.

Figure 4:
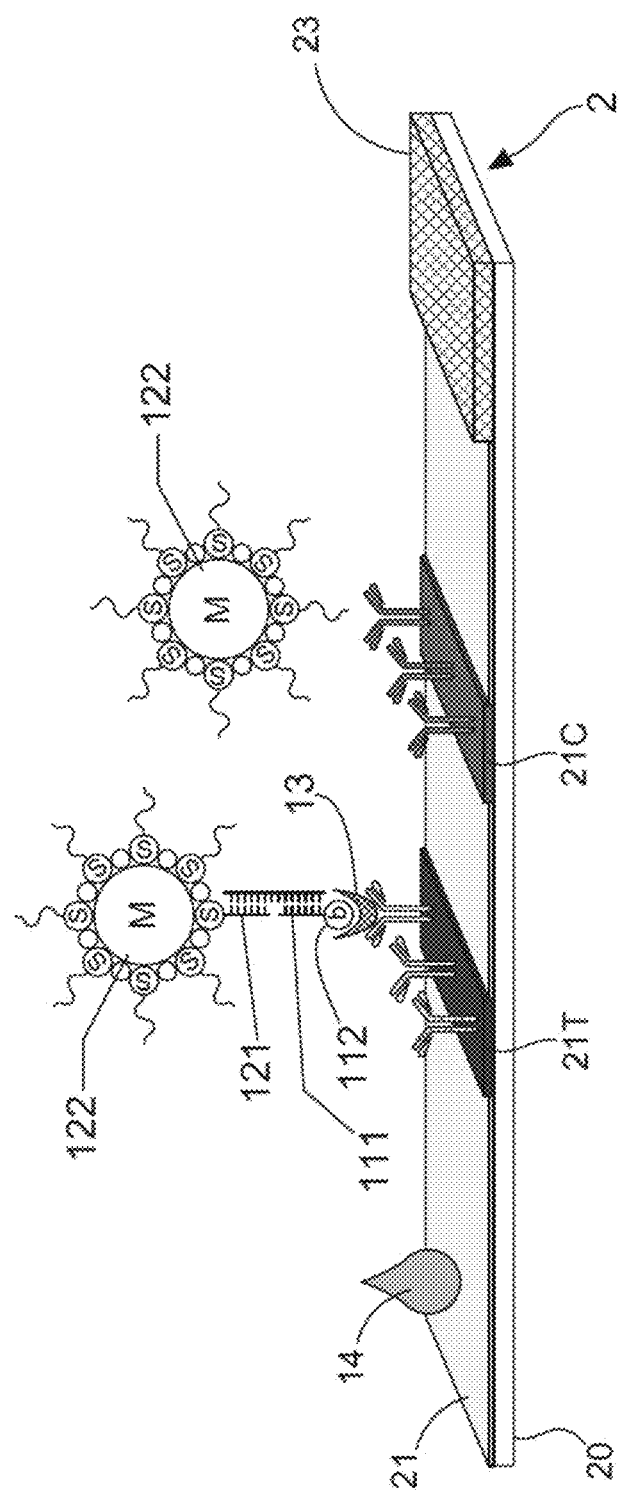
FIG. 4 shows a second schematic stereo diagram of the lateral flow strip.

FIG. 4 shows a second schematic stereo diagram of the lateral flow strip. As FIG. 4 shows, the absorption pad 23 provides a driving force for making the test sample laterally move toward the test line 21T. When the test sample reaches the test line 21T, hybrid complex constituted by the capture probe 11, the detection probe 12 and the single-stranded DNA is fixed at the test line 21T because the biotin (i.e., the combiner 112) is captured by the anti-streptavidin antibody (i.e., the first capture antibody). Moreover, after there are more and more hybrid complex accumulated on the test line 21T, a first colored line (red band) shows up in the region of the test line 21T. Furthermore, the test sample continuously moves toward the control line 21C. When the test sample reaches the control line 21C, hybrid complex is fixed at the control line 21C because the detection probe 12 is captured by the anti-BSA antibody (i.e., the second capture antibody). Moreover, after there are more and more hybrid complex accumulated on the control line 21C, a second colored line (red band) shows up in the region of the control line 21C.

Sensitivity of BKV Detection of the Nucleic Acid Lateral Flow Immunoassay

Figure 5:
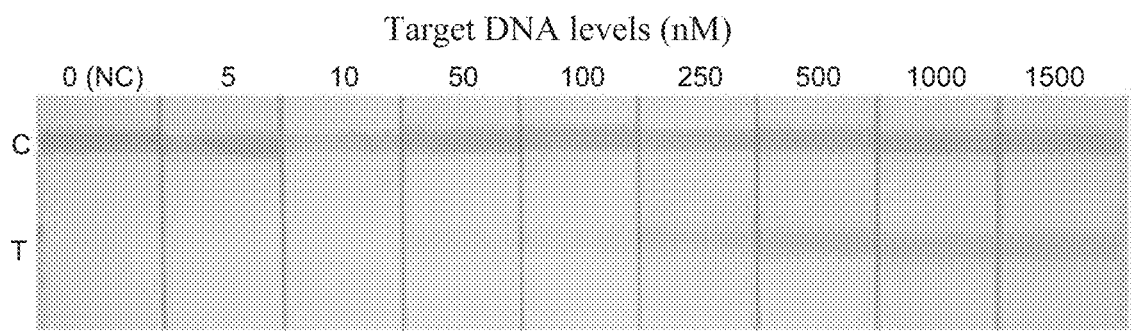
FIG. 5 shows nine real images of the lateral flow strip.
Figure 6:
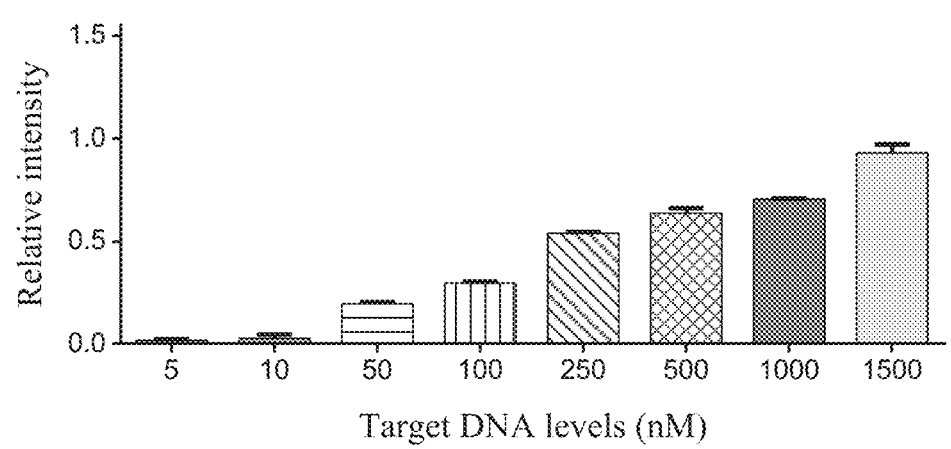
FIG. 6 shows a bar chart of target DNA levels (nM) versus T/C ratio values by relative intensity.

FIG. 5 shows nine real images of the lateral flow strip. According to the nine real images, it is known that, in case of the BKV DNA level contained in the test sample reaching 50 nM, the red band showing up in the test line 21T and the red band showing up in the control line 21C are both recognizable by human eyes. Of course, in case of the BKV DNA level being below 50 nM, an optical reader (e.g., a smartphone installed with a lateral flow assay reader App) can be used to read out a T/C ratio value from the test line 21T and the control line 21C. FIG. 6 shows a statistical bar chart of target (i.e., BKV) DNA levels (nM) versus T/C ratio values (labeled by relative intensity) that are measured by using the optical reader. Therefore, according to the data of FIG. 6, it is understood that the nucleic acid lateral flow immunoassay of the present invention exhibits a linear range of detection for BKV, and the linear range of detection is in a range between 5 nM and 500 nM.

Specificity of BKV Detection of the Nucleic Acid Lateral Flow Immunoassay

Figure 7:
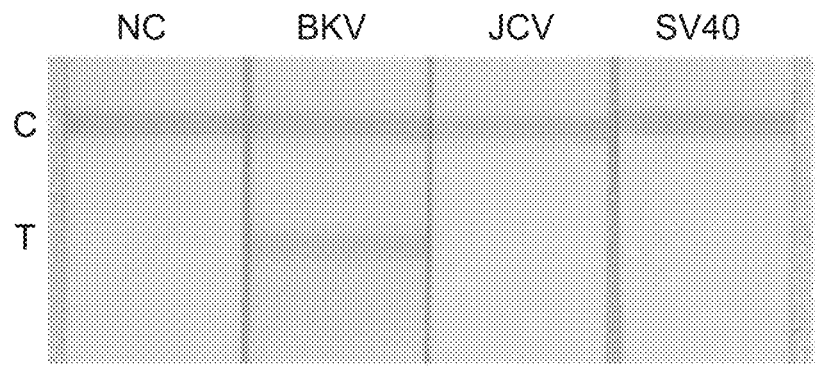
FIG. 7 shows four real images of the lateral flow strip.
Figure 8:
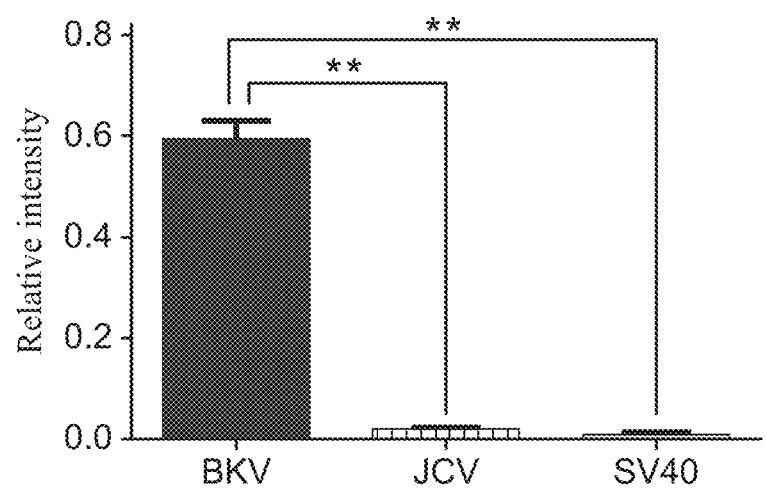
FIG. 8 shows a bar chart of different virus versus T/C ratio values by relative intensity.

FIG. 7 shows four real images of the lateral flow strip, and FIG. 8 shows a statistical bar chart of different virus (BKV, JCV, and SV40) versus T/C ratio values (labeled by relative intensity) that are measured by using the optical reader. From experimental data of FIG. 7 and FIG. 8, it is clear that the nucleic acid lateral flow immunoassay shows specificity on BKV detection. Therefore, experimental data have proved that, the nucleic acid lateral flow immunoassay of the present invention can be adopted for conducting BK virus detection on a sample that is collected from environmental water, sewage water, drinking water, urine, or serum.

Figure 9:
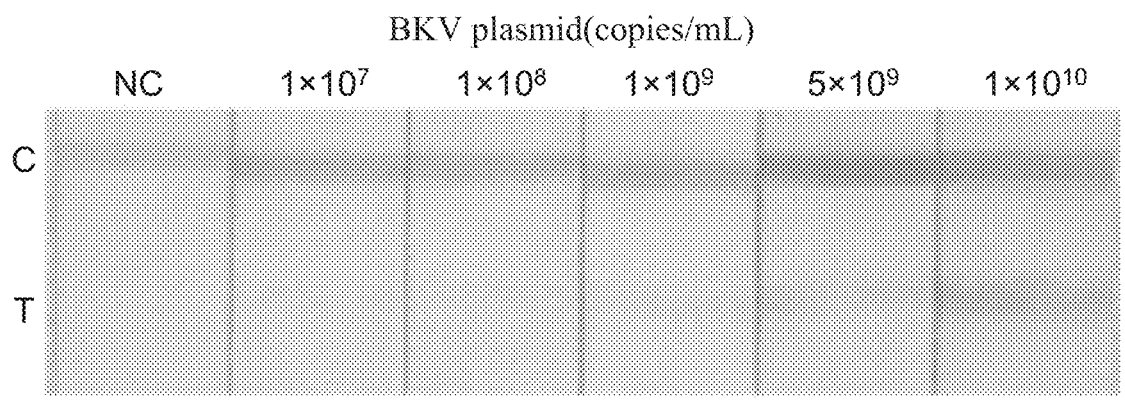
FIG. 9 shows six real images of the lateral flow strip.
Figure 10:
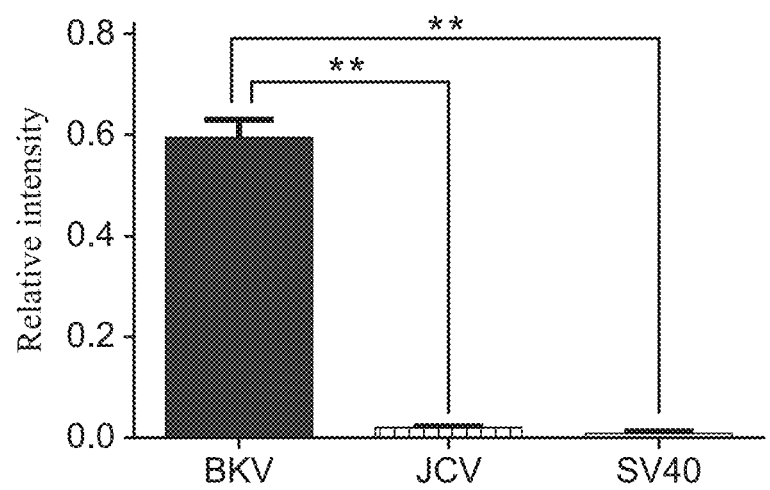
FIG. 10 shows a bar chart of different virus versus T/C ratio values by relative intensity.

Adopting the Nucleic Acid Lateral Flow Immunoassay to Detect Plasmid DNA of BK Virus FIG. 9 shows six real images of the lateral flow strip. According to the six real images, it is known that, in case of the plasmid DNA level contained in the test sample reaching $10^8$ copies/mL, the red band showing up in the test line 21T and the red band showing up in the control line 21C are both recognizable by human eyes. Of course, in case of the plasmid DNA being below $10^8$ copies/mL, an optical reader (e.g., a smartphone installed with a lateral flow assay reader App) can be used to read out a T/C ratio value from the test line 21T and the control line 21C. FIG. 10 shows a statistical bar chart of different virus versus T/C ratio values (labeled by relative intensity) that are measured by using the optical reader. Therefore, according to the data of FIG. 9 and FIG. 10, it is understood that the nucleic acid lateral flow immunoassay of the present invention exhibits a detection range of plasmid DNA of BK virus, and the detection range is in a range between $10^7$ copies/mL and $10^{10}$ copies/mL. As a result, experimental data have proved that the nucleic acid lateral flow immunoassay of the present invention shows a clinical significance on BK virus detection.

Nowadays, BK virus is found to exist in natural water and home sewage water. For this reason, BK virus has become one of a pathogenic indicator of sewage water and natural water defined in the United Nations World Water Development Report (UN WWDR). It is worth mentioning that, experimental data have proved that, the nucleic acid lateral flow immunoassay can be adopted for conducting a BK virus detection on a sample that is collected from environmental water, sewage water, drinking water, urine, or serum.

Moreover, when adopting the nucleic acid lateral flow immunoassay of the present invention to carry out a BKV detection, a sample for the BKV detection is not needed to be applied with a PCR process and/or a RPA process. Moreover, there is no RNA transcription process conducted during the operation of the BKV detection. Therefore, the nucleic acid lateral flow immunoassay disclosed by the present invention including advantages of low cost, achieving rapid BKV detection, and able to be conducted by common people, able to be used in BKV detection without needing using any professional machine.

Therefore, through above descriptions, all embodiments and their constituting elements of the nucleic acid probe set and the nucleic acid lateral flow immunoassay using the same according to the present invention have been introduced completely and clearly. The above description is made on embodiments of the present invention. However, the embodiments are not intended to limit scope of the present invention, and all equivalent implementations or alterations within the spirit of the present invention still fall within the scope of the present invention.

What is claimed is:

1. A nucleic acid probe set, comprising:
   a capture probe, comprising a first nucleotide sequence that comprises at least 19 nucleotide bases and a combiner connected to one terminal base of the first nucleotide sequence; and
   a detection probe, comprising a second nucleotide sequence that comprises at least 19 nucleotide bases and a label connected to one terminal base of the second nucleotide sequence;
   wherein the first nucleotide sequence and the second nucleotide sequence
   comprise a nucleotide sequence of 5'-GAAAGGAAGGTAAGTTGTTAAG-3' (SEQ ID NO:8) and 5'-TATGTATGAATAGAGTCTTAGGT-3' (SEQ ID NO:7), respectively, or vice versa.

2. The nucleic acid probe set of claim 1, wherein the combiner is a biotin that is used to combine with a streptavidin (SA), and the label being made of a fluorescent material that is selected from a group consisting of gold nanoparticles, silver nanoparticles, carbon nanoparticles, quantum dots (QDs), colloidal gold, colloidal silver, and colloidal QDs.

3. The nucleic acid probe set of claim 1, wherein the terminal base of the first nucleotide sequence connected with the combiner is a 5'-terminal base or a 3'-terminal base, the terminal base of the second nucleotide sequence connected with the label is a 5'-terminal base or a 3'-terminal base.

4. The nucleic acid probe set of claim 1, wherein the capture probe further comprises a spacer that is connected between the terminal base and the combiner, and the spacer comprises 10 adenines.

5. The nucleic acid probe set of claim 1, wherein the detection probe further comprises a spacer connected to the terminal base and a thiol group connected between the spacer and the label, and the spacer comprises 10 adenines.

6. The nucleic acid probe set of claim 1, wherein the label is made of gold nanoparticles having a particle size in a range between 25 nm and 65 nm.

7. A nucleic acid lateral flow immunoassay for detecting BK virus, comprising: a lateral flow strip and a tetrameric protein solution for solving a sample; characterised in that the nucleic acid lateral flow immunoassay further comprising:
   a capture probe for being mixed in a test solution consisting of the tetrameric protein solution and the sample, comprising a first nucleotide sequence that comprises at least 19 nucleotide bases and a combiner connected to one terminal base of the first nucleotide sequence; and
   a detection probe for being mixed in a test sample, comprising a second nucleotide sequence that comprises at least 19 nucleotide bases and a label connected to one terminal base of the second nucleotide sequence; wherein the first nucleotide sequence and the second nucleotide sequence comprise a nucleotide sequence of 5' GAAAGGAAGGTAAGTTGTTAAG-3' (SEQ ID NO:8) and 5'-TATGTATGAATAGAGTCTTAGGT-3' (SEQ ID NO:7), respectively, or vice versa.

8. The nucleic acid lateral flow immunoassay of claim 7, wherein the tetrameric protein solution comprising a buffer liquid and a tetrameric protein dissolved or dispersed in the buffer liquid.

9. The nucleic acid lateral flow immunoassay of claim 8, wherein the tetrameric protein is a streptavidin (SA), and the buffer liquid is a phosphate buffer solution.

10. The nucleic acid lateral flow immunoassay of claim 7, wherein the lateral flow strip further comprises:
    a supporting substrate, wherein a membrane substrate is disposed on the supporting substrate; and
    an absorption pad, being formed on the supporting substrate, and being located at a rear-end side of the supporting substrate.

11. The nucleic acid lateral flow immunoassay of claim 10, wherein the membrane substrate is made of a material that is selected from a group consisting of nitrocellulose (NC), polyvinylidene difluoride (PVDF) and nylon.

12. The nucleic acid lateral flow immunoassay of claim 7, wherein the combiner is a biotin, and the label is made of a fluorescent material that is selected from a group consisting of gold nanoparticles, silver nanoparticles, carbon nanoparticles, quantum dots (QDs), colloidal gold, colloidal silver, and colloidal QDs.

13. The nucleic acid lateral flow immunoassay of claim 7, wherein the terminal base of the first nucleotide sequence connected with the combiner is a 5'-terminal base or a 3'-terminal base, the terminal base of the second nucleotide sequence connected with the label is a 5'-terminal base or a 3'-terminal base.

14. The nucleic acid lateral flow immunoassay of claim 7, wherein the capture probe further comprises a spacer that is connected between the terminal base and the combiner, and the spacer comprises adenines.

15. The nucleic acid lateral flow immunoassay of claim 7, wherein the detection probe further comprises a spacer connected to the terminal base and a thiol group connected between the spacer and the label, and the spacer comprises adenines.

* * * * *